(12) United States Patent
Veyland et al.

(10) Patent No.: US 9,034,969 B2
(45) Date of Patent: May 19, 2015

(54) RUBBER COMPOSITION COMPRISING A THIAZOLINE

(75) Inventors: Anne Veyland, Marsat (FR); Nicolas Seeboth, Clermont-Ferrand (FR); José Carlos Araujo Da Silva, Pont du Chateau (FR)

(73) Assignees: Michelin Recherche et Technique S.A., Granges-Paccot (CH); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 244 days.

(21) Appl. No.: 13/501,071

(22) PCT Filed: Oct. 8, 2010

(86) PCT No.: PCT/EP2010/065074
§ 371 (c)(1),
(2), (4) Date: Sep. 25, 2012

(87) PCT Pub. No.: WO2011/042526
PCT Pub. Date: Apr. 14, 2011

(65) Prior Publication Data
US 2013/0053504 A1    Feb. 28, 2013

(30) Foreign Application Priority Data
Oct. 8, 2009 (FR) ..................................... 09 57041

(51) Int. Cl.
*B60C 1/00* (2006.01)
*C08K 5/46* (2006.01)
*C07D 277/16* (2006.01)
*C08K 5/00* (2006.01)
*C08K 5/23* (2006.01)
*C08L 7/00* (2006.01)
*C08L 9/06* (2006.01)
*C08L 21/00* (2006.01)

(52) U.S. Cl.
CPC ................. *C08K 5/46* (2013.01); *B60C 1/0016* (2013.04); *C07D 277/16* (2013.01); *C08K 5/0025* (2013.01); *C08K 5/23* (2013.01); *C08L 7/00* (2013.01); *C08L 9/06* (2013.01); *C08L 21/00* (2013.01)

(58) Field of Classification Search
USPC .................................................... 524/526, 492
See application file for complete search history.

(56) References Cited

U.S. PATENT DOCUMENTS 2,779,809 A    1/1957    Carr
2005/0267247 A1*    12/2005    Steger et al. .................. 524/492

FOREIGN PATENT DOCUMENTS

EP    1600472    11/2005

* cited by examiner

*Primary Examiner* — Ling Choi
*Assistant Examiner* — Thuy-Ai Nguyen
(74) *Attorney, Agent, or Firm* — Cozen O'Connor

(57) ABSTRACT

A rubber composition for the manufacture of tires, based on a blend of at least one diene elastomer chosen from natural rubber and synthetic polyisoprene and of one or more diene elastomers chosen from the group consisting of polybutadienes, butadiene copolymers and isoprene copolymers, on one or more reinforcing fillers and on a vulcanization system, the said vulcanization system comprising one or more thiazoline compounds of formula:

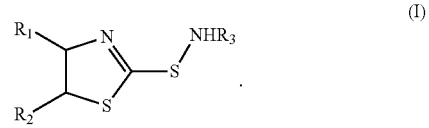

(I)

16 Claims, No Drawings

RUBBER COMPOSITION COMPRISING A THIAZOLINE

RELATED APPLICATIONS

This is a U.S. national stage of application No. PCT/EP2010/065074, filed on Oct. 8, 2010. Priority is claimed on the following application: French Application No. 0957041 filed on Oct. 8, 2009, the disclosure content of which is hereby incorporated here by reference.

FIELD OF THE INVENTION

The present invention relates to a rubber composition which can be used in particular in the manufacture of tires or semi-finished products for tires, such as treads, the said composition being based on a blend of specific diene elastomers, on a reinforcing filler and on a vulcanization system comprising a specific thiazoline compound.

BACKGROUND OF THE INVENTION

The vulcanization of diene elastomers by sulphur is widely used in the rubber industry, in particular in the tire industry. The principle of vulcanization lies in the creation of sulphur bridges between two macromolecules by reaction with the double bonds of these diene elastomers.

Use is made, to vulcanize diene elastomers, of a relatively complex vulcanization system comprising, in addition to sulphur, a primary vulcanization accelerator, such as sulphenamides comprising a benzothiazole ring system, and various secondary vulcanization accelerators or vulcanization activators, very particularly zinc derivatives, such as zinc oxide (ZnO), alone or used with fatty acids.

The sulphenamides comprising a benzothiazole ring system used as primary vulcanization accelerators are, for example, N-cyclohexyl-2-benzothiazolesulphenamide (abbreviated to "CBS"), N,N-dicyclohexyl-2-benzothiazolesulphenamide (abbreviated to "DCBS"), N-tert-butyl-2-benzothiazolesulphenamide (abbreviated to "TBBS") and the mixtures of these compounds.

However, vulcanization with sulphur has the known disadvantage of resulting in limited resistance of the vulcanizates obtained due to the thermal ageing of the latter. In particular, the vulcanizates of diene elastomers crosslinked starting from sulphur exhibit high sensitivity to the temperature when the latter reaches a value in the vicinity of the initial curing or vulcanization temperature. This results in a fall in the density of the sulphur bridges initially formed during the vulcanization, the distribution of the vulcanization network changing in the direction of shortening, that is to say a decrease in the polysulphide bridges to the advantage of the monosulphide bridges. This phenomenon, known under the term of reversion, is accompanied by deterioration in the mechanical properties of the vulcanizates.

SUMMARY OF THE INVENTION

One object of the invention is to provide novel rubber compositions, which can be used in particular in the manufacture of tires, especially treads, which exhibit an improved resistance to reversion.

Another object of the invention is to have the other rheometric, rheological, dynamic, mechanical and plasticity properties of these compositions remain comparable, indeed even to be improved, with respect to the properties of the known compositions, in particular with regard to the rolling resistance/wear compromise.

One aspect of the invention is directed to a rubber composition for the manufacture of tires, based on a blend of at least one diene elastomer chosen from natural rubber and synthetic polyisoprene and of one or more diene elastomers chosen from the group consisting of polybutadienes, butadiene copolymers and isoprene copolymers, on one or more reinforcing fillers and on a vulcanization system, the said vulcanization system comprising one or more thiazoline compounds of formula:

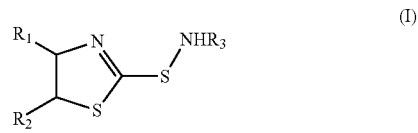

(I)

where
$R_1$ and $R_2$ independently represent H or a $C_1$-$C_{25}$-hydrocarbon group chosen from linear, branched or cyclic alkyl groups and aryl groups, optionally interrupted by one or more heteroatoms, it being possible for $R_1$ and $R_2$ to together form a ring,
$R_3$ represents:
  a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
  a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

Such a thiazoline compound is known from the document U.S. Pat. No. 2,700,659 as vulcanization accelerator in natural rubber compositions. This document is not concerned with compositions comprising a blend of natural rubber and of another elastomer and a fortiori a blend of at least one diene elastomer chosen from natural rubber and synthetic polyisoprene and of one or more diene elastomers chosen from the group consisting of polybutadienes, butadiene copolymers and isoprene copolymers.

Another aspect of the invention is directed to a process for preparing a rubber composition for the manufacture of tires according to an embodiment of the invention, characterized in that it comprises the following stages:
  incorporating the reinforcing filler or fillers in the natural rubber and synthetic diene elastomer or elastomers, during a first "non-productive" stage, everything being kneaded thermomechanically, in one or more goes, until a maximum temperature of between 130° C. and 200° C. is reached,
  cooling the combined mixture to a temperature of less than 100° C.,
  subsequently incorporating, during a second "productive" stage, the vulcanization system and then
  kneading everything up to a maximum temperature of less than 120° C.

Another aspect of the invention is directed to the use of a composition according to an embodiment of the invention in the manufacture of a finished article or a semi-finished product intended for a motor vehicle ground-contact system, such as tire, internal tire safety support, wheel, rubber spring, elastomeric joint or other suspension and anti-vibratory element. In particular, the composition according to the invention can be used in the manufacture of semi-finished rubber products intended for tires, such as treads, crown reinforcing plies, sidewalls, carcass reinforcing plies, beads, protectors, underlayers, rubber blocks and other internal rubbers, in particular decoupling rubbers, intended to provide the bonding or the interface between the abovementioned regions of the tires.

A further aspect of the invention is directed to a finished article or semi-finished product intended for a motor vehicle ground-contact system, in particular the tires and semi-finished products for tires comprising a composition according to an embodiment of the invention. The tires in accordance with the invention are intended in particular for passenger vehicles as well as for industrial vehicles chosen from vans, heavy-duty vehicles—i.e., underground, bus, heavy road transport vehicles (lorries, tractors, trailers) or off-road vehicles—, agricultural vehicles or earth-moving equipment, aircraft, or other transportation or handling vehicles.

A final aspect of the invention is a blend of at least one diene elastomer chosen from natural rubber and synthetic polyisoprene and of the use as vulcanization accelerator, in a composition based on one or more diene elastomers chosen from the group consisting of polybutadienes, butadiene copolymers and isoprene copolymers, on one or more reinforcing fillers and on a vulcanization system, of one or more thiazoline compounds of formula (I).

DETAILED DISCUSSION

The invention and its advantages will be easily understood in the light of the description and implementation examples which follow.

I. Measurements and Tests Used

The rubber compositions, in which the thiazoline vulcanization accelerators are tested, are characterized, before and after curing, as indicated below.

Rheometry

The measurements are carried out at 150° C. with an oscillating disc rheometer, according to Standard DIN 53529—part 3 (June 1983). The change in the rheometric torque, ΔTorque, as a function of time describes the change in the stiffening of the composition as a result of the vulcanization reaction. The measurements are processed according to Standard DIN 53529—part 2 (March 1983): $t_0$ is the induction period, that is to say the time necessary for the start of the vulcanization reaction; $t_\alpha$ (for example $t_{99}$) is the time necessary to achieve a conversion of $\alpha\%$, that is to say $\alpha\%$ (for example 99%) of the difference between the minimum and maximum torques. The conversion rate constant, denoted K (expressed in $min^{-1}$), which is 1st order, calculated between 30% and 80% conversion, which makes it possible to assess the vulcanization kinetics, is also measured.

Measurement of the Reversion

The reversion can be analysed according to different methods, the aim being to determine, indirectly, the change in the density of the sulphur bridges between a curing "at the optimum" (corresponding to the maximum torque $C_{max}$) and a prolonged curing.

One approach consists in measuring the change (reduction) in the rheometric torque: the parameter $\Delta R_{120}$ represents the change in % in the torque between $C_{max}$ and the torque measured after curing for 120 minutes, at a specific curing temperature (for example, 150° C.). The greater the parameter $\Delta R_{120}$, the more significant the reversion phenomenon.

II. Conditions for the Implementation of the Invention

As explained above, the composition according to the invention is based on a blend of at least one diene elastomer chosen from natural rubber and synthetic polyisoprene and of one or more diene elastomers chosen from the group consisting of polybutadienes, butadiene copolymers and isoprene copolymers, on one or more reinforcing fillers and on a vulcanization system.

The expression composition "based on" should be understood as meaning a composition comprising the mixture and/or the reaction product of the various constituents used, some of these base constituents being capable of reacting or intended to react with one another, at least in part, during the various phases of manufacture of the composition, in particular during its vulcanization.

In the present description, unless expressly indicated otherwise, all the percentages (%) are percentages by weight. Moreover, any interval of values denoted by the expression "between a and b" represents the range of values extending from greater than a to less than b (i.e., limits a and b excluded), whereas any interval of values denoted by the expression "from a to b" means the range of values extending from a up to b (i.e., including the strict limits a and b).

II-1. Diene Elastomer

As explained above, the composition according to the invention is based on at least one diene elastomer chosen from natural rubber and synthetic polyisoprene and on one or more diene elastomers chosen from the group consisting of polybutadienes, butadiene copolymers and isoprene copolymers.

The term "diene" elastomer or rubber should be understood as meaning, in a known way, an elastomer resulting at least in part (i.e., a homopolymer or a copolymer) from diene monomers (monomers carrying two carbon-carbon double bonds which may or may not be conjugated).

These diene elastomers can be classified into two categories: "essentially unsaturated" or "essentially saturated". The term "essentially unsaturated" is understood to mean generally a diene elastomer resulting at least in part from conjugated diene monomers having a level of units of diene origin (conjugated dienes) which is greater than 15% (molar %); thus it is that diene elastomers such as butyl rubbers or copolymers of dienes and of α-olefins of EPDM type do not come within the preceding definition and can in particular be described as "essentially saturated" diene elastomers (low or very low level of units of diene origin, always less than 15%). In the category of "essentially unsaturated" diene elastomers, the term "highly unsaturated" diene elastomer is understood to mean in particular a diene elastomer having a level of units of diene origin (conjugated dienes) which is greater than 50%.

Given these definitions, the term diene elastomer capable of being used in the compositions in accordance with the invention is understood more particularly to mean:

(a)—any homopolymer obtained by polymerization of a conjugated diene monomer having from 4 to 12 carbon atoms;

(b)—any copolymer obtained by copolymerization of one or more conjugated dienes with one another or with one or more vinylaromatic compounds having from 8 to 20 carbon atoms;

(c)—a ternary copolymer obtained by copolymerization of ethylene and of an α-olefin having from 3 to 6 carbon atoms with a non-conjugated diene monomer having from 6 to 12 carbon atoms, such as, for example, the elastomers obtained from ethylene and propylene with a non-conjugated diene monomer of the abovementioned type, such as, in particular, 1,4-hexadiene, ethylidenenorbornene or dicyclopentadiene;

(d)—a copolymer of isobutene and of isoprene (butyl rubber) and also the halogenated versions, in particular chlorinated or brominated versions, of this type of copolymer.

Although it applies to any type of diene elastomer, a person skilled in the art of tires will understand that the present invention is preferably employed with essentially unsaturated diene elastomers, in particular of the type (a) or (b) above.

The following are suitable in particular as conjugated dienes: 1,3-butadiene, 2-methyl-1,3-butadiene, 2,3-di($C_1$-$C_5$ alkyl)-1,3-butadienes, such as, for example, 2,3-dimethyl-1,3-butadiene, 2,3-diethyl-1,3-butadiene, 2-methyl-3-ethyl-1,3-butadiene or 2-methyl-3-isopropyl-1,3-butadiene, an aryl-1,3-butadiene, 1,3-pentadiene or 2,4-hexadiene. The following, for example, are suitable as vinylaromatic compounds: styrene, ortho-, meta- or para-methylstirene, the "vinyltoluene" commercial mixture, para-(tert-butyl)stirene, methoxystirenes, chlorostirenes, vinylmesitylene, divinylbenzene or vinylnaphthalene.

The copolymers can comprise between 99% and 20% by weight of diene units and between 1% and 80% by weight of vinylaromatic units. The elastomers can have any microstructure which depends on the polymerization conditions used, in particular on the presence or absence of a modifying and/or randomizing agent and on the amounts of modifying and/or randomizing agent employed. The elastomers can, for example, be block, random, sequential or microsequential elastomers and can be prepared in dispersion, in emulsion or in solution; they can be coupled and/or star-branched or also functionalized with a coupling and/or star-branching or functionalization agent. For coupling with carbon black, mention may be made, for example, of functional groups comprising a C—Sn bond or of aminated functional groups, such as aminobenzophenone, for example; for coupling with a reinforcing inorganic filler, such as silica, mention may be made, for example, of silanol functional groups or polysiloxane functional groups having a silanol end (such as described, for example, in FR 2 740 778, U.S. Pat. No. 6,013,718 or WO 2008/141702), of alkoxysilane groups (such as described, for example, in FR 2 765 882 or U.S. Pat. No. 5,977,238), of carboxyl groups (such as described, for example, in WO 01/92402, U.S. Pat. No. 6,815,473, WO 2004/096865 or US 2006/0089445) or of polyether groups (such as described, for example, in EP 1 127 909, U.S. Pat. No. 6,503,973, WO 2009/000750 or WO 2009/000752). Mention may also be made, as other examples of functionalized elastomers, of elastomers (such as SBR, BR, NR or IR) of the epoxidized type.

The following are suitable: polybutadienes, in particular those having a content (molar %) of 1,2-units of between 4% and 80% or those having a content (molar %) of cis-1,4-units of greater than 80%, polyisoprenes, butadiene/stirene copolymers and in particular those having a Tg (glass transition temperature, measured according to ASTM D3418) of between 0° C. and −70° C. and more particularly between −10° C. and −60° C., a stirene content of between 5% and 60% by weight and more particularly between 20% and 50%, a content (molar %) of 1,2-bonds of the butadiene part of between 4% and 75% and a content (molar %) of trans-1,4-bonds of between 10% and 80%, butadiene/isoprene copolymers, in particular those having an isoprene content of between 5% and 90% by weight and a Tg of −40° C. to −80° C., or isoprene/stirene copolymers, in particular those having a stirene content of between 5% and 50% by weight and a Tg of between 5° C. and −50° C. In the case of butadiene/stirene/isoprene copolymers, those having a stirene content of between 5% and 50% by weight and more particularly of between 10% and 40%, an isoprene content of between 15% and 60% by weight and more particularly of between 20% and 50%, a butadiene content of between 5% and 50% by weight and more particularly of between 20% and 40%, a content (molar %) of 1,2-units of the butadiene part of between 4% and 85%, a content (molar %) of trans-1,4-units of the butadiene part of between 6% and 80%, a content (molar %) of 1,2- plus 3,4-units of the isoprene part of between 5% and 70% and a content (molar %) of trans-1,4-units of the isoprene part of between 10% and 50%, and more generally any butadiene/stirene/isoprene copolymer having a Tg of between −5° C. and −70° C., are suitable in particular.

To sum up, the diene elastomer or elastomers of the composition according to the invention are chosen from natural rubber and/or synthetic polyisoprene, that is to say an isoprene homopolymer, blended with elastomers preferably chosen from the group of the highly unsaturated diene elastomers consisting of polybutadienes (abbreviated to "BR"), butadiene copolymers, isoprene copolymers and the mixtures of these elastomers. Such copolymers are more preferably chosen from the group consisting of butadiene/stirene copolymers (SBR), isoprene/butadiene copolymers (BIR), isoprene/stirene copolymers (SIR) and isoprene/butadiene/stirene copolymers (SBIR).

According to a specific embodiment, the composition according to the invention is based on a blend of natural rubber and/or synthetic polyisoprene with one or more polybutadienes and one or more SBRs, whether an SBR prepared in emulsion ("ESBR") or an SBR prepared in solution ("SSBR"). In the case of an SBR (ESBR or SSBR) elastomer, use is made in particular of an SBR having a moderate stirene content, for example of between 20% and 35% by weight, or a high stirene content, for example from 35% to 45%, a content of vinyl bonds of the butadiene part of between 15% and 70%, a content (molar %) of trans-1,4-bonds of between 15% and 75% and a Tg of between −10° C. and −55° C.

More particularly, the composition according to the invention can also be based on a blend of natural rubber, a butadiene/stirene copolymer and a polybutadiene (NR/SBR/BR). Preferably, the natural rubber represents from 30 to 60 phr, the polybutadiene or polybutadienes represent from 10 to 30 phr and the butadiene/stirene copolymer or copolymers represent from 30 to 60 phr.

The synthetic diene elastomer or elastomers present in the composition according to the invention blended with the natural rubber can also be used in combination with any type of synthetic elastomer other than a diene elastomer, indeed even with polymers other than elastomers, for example thermoplastic polymers.

II-2. Reinforcing Filler

Use may be made of any type of reinforcing filler known for its capabilities of reinforcing a rubber composition which can be used in the manufacture of tires, for example an organic filler, such as carbon black, a reinforcing inorganic filler, such as silica, or a blend of these two types of filler, in particular a blend of carbon black and silica.

All carbon blacks, in particular blacks of the HAF, ISAF or SAF type, conventionally used in tires ("tire-grade" blacks) are suitable as carbon blacks. Mention will more particularly be made, among the latter, of the reinforcing carbon blacks of the 100, 200 or 300 series (ASTM grades), such as, for example, the N115, N134, N234, N326, N330, N339, N347 or N375 blacks, or also, depending on the applications targeted, the blacks of higher series (for example, N660, N683 or N772). The carbon blacks might, for example, be already incorporated in the isoprene elastomer in the form of a masterbatch (see, for example, Applications WO 97/36724 or WO 99/16600).

Mention may be made, as examples of organic fillers other than carbon blacks, of the functionalized polyvinylaromatic organic fillers as described in Applications WO-A-2006/069792 and WO-A-2006/069793.

The term "reinforcing inorganic filler" should be understood, in the present patent application, by definition, as meaning any inorganic or mineral filler, whatever its colour and its origin (natural or synthetic), also known as "white filler", "clear filler" or even "non-black filler", in contrast to carbon black, capable of reinforcing by itself alone, without means other than an intermediate coupling agent, a rubber composition intended for the manufacture of tires, in other words capable of replacing, in its reinforcing role, a conventional tire-grade carbon black; such a filler is generally characterized, in a known way, by the presence of hydroxyl (—OH) groups at its surface.

The physical state under which the reinforcing inorganic filler is provided is not important, whether it is in the form of a powder, of microbeads, of granules, of beads or any other appropriate densified form. Of course, the term reinforcing inorganic filler is also understood to mean mixtures of different reinforcing inorganic fillers, in particular of highly dispersible siliceous and/or aluminous fillers as described below.

Mineral fillers of the siliceous type, in particular silica ($SiO_2$), or of the aluminous type, in particular alumina ($Al_2O_3$), are suitable in particular as reinforcing inorganic fillers. The silica used can be any reinforcing silica known to a person skilled in the art, in particular any precipitated or pyrogenic silica exhibiting a BET surface and a CTAB specific surface both of less than 450 $m^2$/g, preferably from 30 to 400 $m^2$/g. Mention will be made, as highly dispersible ("HDS") precipitated silicas, for example, of the Ultrasil 7000 and Ultrasil 7005 silicas from Degussa, the Zeosil 1165 MP, 1135 MP and 1115 MP silicas from Rhodia, the Hi-Sil EZ150G silica from PPG, the Zeopol 8715, 8745 and 8755 silicas from Huber or the silicas with a high specific surface as described in Application WO 03/16837.

When the composition according to the invention is intended for tire treads having a low rolling resistance, the reinforcing inorganic filler used, in particular if it is silica, preferably has a BET surface of between 45 and 400 $m^2$/g, more preferably of between 60 and 300 $m^2$/g.

Preferably, the level of total reinforcing filler (carbon black and/or reinforcing inorganic filler, such as silica) is between 20 and 200 phr, more preferably between 30 and 150 phr, the optimum being in a known way different depending on the specific applications targeted: the level of reinforcement expected with regard to a bicycle tire, for example, is, of course, less than that required with regard to a tire capable of running at high speed in a sustained manner, for example a motorcycle tire, a tire for a passenger vehicle or a tire for a utility vehicle, such as a heavy duty vehicle.

According to a preferred embodiment of the invention, use is made of carbon black as reinforcing filler.

According to another embodiment of the invention, use is made of a reinforcing filler comprising between 30 and 150 phr, more preferably between 50 and 120 phr, of inorganic filler, particularly silica, and optionally carbon black; the carbon black, when it is present, is preferably used at a level of less than 20 phr, more preferably of less than 10 phr (for example, between 0.1 and 10 phr).

In order to couple the reinforcing inorganic filler to the diene elastomer, use is made, in a known way, of an at least bifunctional coupling agent (or bonding agent) intended to provide a satisfactory connection, of chemical and/or physical nature, between the inorganic filler (surface of its particles) and the diene elastomer, in particular bifunctional organosilanes or polyorganosiloxanes.

Use is made in particular of silane polysulphides, referred to as "symmetrical" or "unsymmetrical" depending on their specific structure, as described, for example, in Applications WO 03/002648 (or US 2005/016651) and WO 03/002649 (or US 2005/016650).

"Symmetrical" silane polysulphides corresponding to the following general formula (III):

$$Z\text{-}A\text{-}S_x\text{-}A\text{-}Z, \qquad (III)$$

in which:
x is an integer from 2 to 8 (preferably from 2 to 5);
A is a divalent hydrocarbon radical (preferably, $C_1$-$C_{18}$ alkylene groups or $C_5$-$C_{12}$ arylene groups, more particularly $C_1$-$C_{10}$, in particular $C_1$-$C_4$, alkylenes, especially propylene);
Z corresponds to one of the formulae below:

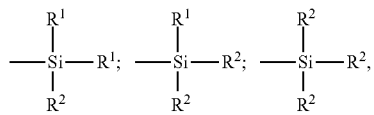

in which:
the $R^1$ radicals, which are unsubstituted or substituted and identical to or different from one another, represent a $C_1$-$C_{18}$ alkyl, $C_5$-$C_{18}$ cycloalkyl or $C_6$-$C_{18}$ aryl group (preferably, $C_1$-$C_5$ alkyl, cyclohexyl or phenyl groups, in particular $C_1$-$C_4$ alkyl groups, more particularly methyl and/or ethyl),
the $R^2$ radicals, which are unsubstituted or substituted and identical to or different from one another, represent a $C_1$-$C_{18}$ alkoxyl or $C_5$-$C_{18}$ cycloalkoxyl group (preferably a group chosen from $C_1$-$C_8$ alkoxyls and $C_5$-$C_8$ cycloalkoxyls, more preferably still a group chosen from $C_1$-$C_4$ alkoxyls, in particular methoxyl and ethoxyl), are suitable in particular, without the above definition being limiting.

In the case of a mixture of alkoxysilane polysulphides corresponding to the above formula (III), in particular the usual mixtures available commercially, the mean value of the "x" index is a fractional number preferably of between 2 and 5, more preferably in the vicinity of 4. However, the invention can also advantageously be carried out, for example, with alkoxysilane disulphides (x=2).

Mention will more particularly be made, as examples of silane polysulphides, of bis(($C_1$-$C_4$)alkoxyl($C_1$-$C_4$)alkylsilyl ($C_1$-$C_4$)alkyl) polysulphides (in particular disulphides, trisulphides or tetrasulphides), such as, for example, bis(3-trimethoxysilylpropyl) or bis(3-triethoxysilylpropyl) polysulphides. Use is in particular made, among these compounds, of bis(3-triethoxysilylpropyl) tetrasulphide, abbreviated to TESPT, of formula $[(C_2H_5O)_3Si\,(CH_2)_3S_2]_2$, or bis (triethoxysilylpropyl) disulphide, abbreviated to TESPD, of formula $[(C_2H_5O)_3Si(CH_2)_3S_2]_2$. Mention will also be made, as preferred examples, of bis(mono($C_1$-$C_4$)alkoxyldi($C_1$-$C_4$) alkylsilylpropyl) polysulphides (in particular disulphides, trisulphides or tetrasulphides), more particularly bis(monoethoxydimethylsilylpropyl) tetrasulphide, as described in Patent Application WO 02/083782 (or US 2004/132880).

Mention will in particular be made, as coupling agent other than alkoxysilane polysulphide, of bifunctional POSs (polyorganosiloxanes) or of hydroxysilane polysulphides ($R^2$=OH in the above formula III), such as described in Patent Applications WO 02/30939 (or U.S. Pat. No. 6,774, 255) and WO 02/31041 (or US 2004/051210), or of silanes or POSs carrying azodicarbonyl functional groups, such as described, for example, in Patent Applications WO 2006/125532, WO 2006/125533 and WO 2006/125534.

In the rubber compositions in accordance with the invention, the content of coupling agent is preferably between 4 and 12 phr, more preferably between 3 and 8 phr.

A person skilled in the art will understand that a reinforcing filler of another nature, in particular organic nature, might be used as filler equivalent to the reinforcing inorganic filler described in the present section, provided that this reinforcing filler is covered with an inorganic layer, such as silica, or else comprises, at its surface, functional sites, in particular hydroxyls, requiring the use of a coupling agent in order to form the connection between the filler and the elastomer.

II.3 Vulcanization System

The vulcanization system proper is based on sulphur (or on a sulphur-donating agent) and on a primary vulcanization accelerator. Additional to this base vulcanization system are various known secondary vulcanization accelerators or vulcanization activators, such as zinc oxide, stearic acid or equivalent compounds, or guanidine derivatives (in particular diphenylguanidine), incorporated during the first non-productive phase and/or during the productive phase, as described subsequently.

The sulphur is used at a preferred level of between 0.5 and 10 phr, more preferably of between 0.5 and 5 phr, in particular between 0.5 and 3 phr, when the composition of the invention is intended, according to a preferred form of the invention, to constitute a tire tread.

The primary vulcanization accelerator must make possible crosslinking of the rubber compositions within industrially acceptable times, while retaining a minimum safety period ("scorch time") during which the compositions can be shaped without the risk of premature vulcanization ("scorching").

According to the invention, the vulcanization system comprises, as primary vulcanization accelerator, one or more thiazoline compounds of formula:

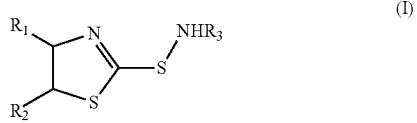

(I)

where $R_1$ and $R_2$ independently represent H or a $C_1$-$C_{25}$-hydrocarbon group chosen from linear, branched or cyclic alkyl groups and aryl groups, optionally interrupted by one or more heteroatoms, it being possible for $R_1$ and $R_2$ to together form a ring, $R_3$ represents:
  a linear or branched $C_1$-$C_{25}$ alkyl group which is optionally interrupted by one or more heteroatoms and which is optionally substituted by one or more cyclic $C_3$-$C_{10}$ alkyl or $C_6$-$C_{12}$ aryl groups, or
  a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

The compounds of formula (I) can advantageously replace, in all or part, the sulphenamide compounds conventionally used.

The term cyclic alkyl group is understood to mean an alkyl group composed of one or more rings.

The heteroatom or heteroatoms can be a nitrogen, sulphur or oxygen atom.

Advantageously, $R_1$ and $R_2$ independently represent H or a methyl group.

According to a specific embodiment, $R_1$ and $R_2$ each represent a hydrogen.

According to a specific embodiment, $R_3$ represents a tert-butyl group.

According to another specific embodiment, $R_3$ represents a cyclic $C_3$-$C_{10}$ alkyl group which is optionally interrupted by one or more heteroatoms and which is optionally substituted by one or more linear, branched or cyclic $C_1$-$C_{25}$ alkyl or $C_6$-$C_{12}$ aryl groups which are optionally interrupted by one or more heteroatoms.

Advantageously, $R_3$ represents a cyclohexyl group.

Hence, a preferred compound of formula (I) is that in which $R_1$ and $R_2$ represent H and $R_3$ represents a cyclohexyl. In this case, the thiazoline compound of formula (I) is N-cyclohexyl-4,5-dihydro-2-thiazolesulphenamide.

The compound or compounds of formula (I) generally represent from 0.1 to 10 phr, preferably from 0.5 to 7 phr and better still from 0.5 to 5 phr (parts by weight per hundred elastomers).

The synthesis of the compounds of formula (I) is well known and is described in particular in the following documents:

U.S. Pat. No. 2,700,659

Journal of Organic Chemistry (1949), 14, 921-34.

The vulcanization system of the composition according to the invention can also comprise one or more additional primary accelerators, in particular the compounds of the family of the thiurams, zinc dithiocarbamate derivatives or thiophosphates.

II-4. Various Additives

The rubber composition according to the invention can also comprise all or a portion of the normal additives generally used in elastomer compositions intended for the manufacture of tires, in particular treads, such as, for example, plasticizing agents or extending oils, whether the latter are aromatic or non-aromatic in nature, pigments, protection agents, such as antiozone waxes (such as Cire Ozone C32 ST), chemical antiozones, antioxidants (such as N-(1,3-dimethylbutyl)-N'-phenyl-p-phenylenediamine), antifatigue agents, reinforcing resins, methylene acceptors (for example, novolac phenolic resin) or methylene donors (for example, HMT or H3M), such as described, for example, in Application WO 02/10269.

Preferably, the composition according to the invention comprises, as preferred non-aromatic or very slightly aromatic plasticizing agent, at least one compound chosen from the group consisting of naphthenic oils, paraffinic oils, MES oils, TDAE oils, glycerol esters (in particular trioleates), plasticizing hydrocarbon resins exhibiting a high Tg preferably of greater than 30° C., and the mixtures of such compounds.

The composition according to the invention can also comprise, in addition to the coupling agents, coupling activators for the reinforcing inorganic filler or more generally processing aids capable, in a known way, by virtue of an improvement in the dispersion of the inorganic filler in the rubber matrix and of a lowering in the viscosity of the compositions, of improving their property of processing in the raw state, these agents being, for example, hydrolysable silanes, such as alkylalkoxysilanes (in particular alkyltriethoxy-silanes), polyols, polyethers (for example, polyethylene glycols), primary, secondary or tertiary amines (for example, trialkanolamines), hydroxylated or hydrolysable POSs, for example α,ω-dihydroxypolyorgano-siloxanes (in particular α,ω-dihydroxypolydimethyl-siloxanes), or fatty acids, such as, for example, stearic acid.

II-5. Manufacture of the Rubber Compositions

The rubber composition according to the invention is manufactured in appropriate mixers using two successive preparation phases according to a general procedure well known to a person skilled in the art: a first phase of thermomechanical working or kneading (sometimes described as "non-productive" phase) at high temperature, up to a maximum temperature of between 130° C. and 200° C., preferably between 145° C. and 185° C., followed by a second phase of mechanical working (sometimes described as "productive" phase) at a lower temperature, typically less than 120° C., for example between 60° C. and 100° C., finishing phase during which the crosslinking or vulcanization system is incorporated.

According to a preferred embodiment of the invention, all the base constituents of the composition of the invention, with the exception of the vulcanization system, namely the reinforcing filler or fillers and the coupling agent, if appropriate, are intimately incorporated, by kneading, in the natural rubber and in the diene elastomer or in the diene elastomers during the first "non-productive" phase, that is to say that at least these various base constituents are introduced into the mixer and are thermomechanically kneaded, in a single stage or several stages, until the maximum temperature of between 130° C. and 200° C., preferably of between 145° C. and 185° C., is reached.

By way of example, the first (non-productive) phase is carried out in a single thermomechanical stage during which all the necessary constituents, the optional additional processing aids and various other additives, with the exception of the vulcanization system, are introduced into an appropriate mixer, such as a normal internal mixer. The total duration of the kneading, in this non-productive phase, is preferably between 1 and 15 min. After cooling the mixture thus obtained during the first non-productive phase, the vulcanization system is then incorporated at low temperature, generally in an external mixer, such as an open mill; everything is then mixed (productive phase) for a few minutes, for example between 2 and 15 min.

The final composition thus obtained is subsequently calendered, for example in the form of a sheet or of a plaque, in particular for characterization in the laboratory, or also extruded in the form of a rubber profiled element which can be used, for example, as a tire tread for a passenger vehicle.

III. Examples of the Implementation of the Invention

In the examples which follow, the invention is implemented with N-cyclohexyl-4,5-dihydro-2-thiazole-sulphenamide (compound A) of following formula:

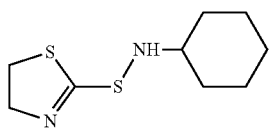

III-1. Synthesis of Thiazoline Compound A

This compound is prepared from 4,5-dihydrothiazole-2-thiol and cyclohexylamine according to the following synthetic scheme:

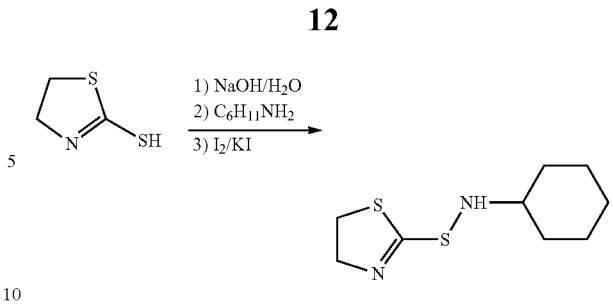

4,5-Dihydrothiazole-2-thiol (CAS number [96-53-7]) is commercially available and is sold, for example, by Aldrich.

The solution of cyclohexylamine (74.98 g, 0.756 mol) in water (100 ml) is added to a solution of 4,5-dihydrothiazole-2-thiol (30.0 g, 0.252 mol) and sodium hydroxide (30.24 g, 0.765 mol) in water (700 ml). The mixture is cooled to +4° C. The iodine solution, prepared by dissolving iodine (63.96 g, 0.252 mol) and potassium iodide (83.66 g, 0.504 mol) in a 600 ml flask made up with demineralised water, is then added dropwise over 2.5-3.0 hours. The reaction medium is subsequently stirred at a temperature of between 0 and +8° C. for one hour.

Subsequently, the precipitate is filtered off and washed with water (3.0 l). The pale-yellow crude product is crystallized from a mixture of pentane and cyclohexane in the ratio by volume of 1:1.

A white solid (28.2 g, 0.130 mol, yield 52.5%) with a melting point of 69.5° C. (lit: 69-70° C.) is obtained.

The molar purity is greater than 98% ($^1$H NMR).

III-2. Preparation of the Compositions

The procedure for the tests which follow is as follows: the natural rubber and the synthetic diene elastomer or elastomers, the reinforcing filler or fillers and the optional coupling agent, followed, after kneading for one to two minutes, by the various other ingredients, with the exception of the vulcanization system, are introduced into an internal mixer, 70% filled and having a starting vessel temperature of approximately 90° C. Thermomechanical working (non-productive phase) is then carried out in one stage (total duration of the kneading equal to approximately 5 min), until a maximum "dropping" temperature of approximately 165° C. is reached. The mixture thus obtained is recovered and cooled, and then in the vulcanization system (sulphur and thiazoline compound) on an external mixer (homofinisher) at 70° C., everything being mixed (productive phase) for approximately 5 to 6 min.

The compositions thus obtained are subsequently calendered, either in the form of plaques (thickness of 2 to 3 mm) or of thin sheets of rubber, for the measurement of their physical or mechanical properties, or in the form of profiled elements which can be used directly, after cutting out and/or assembling to the desired dimensions, for example as semi-finished products for tires, in particular as tire treads.

III-3. Characterization Tests—Results

The object of this example is to compare the properties of a rubber composition according to the invention (composition 4), which can be used in the manufacture of a tire tread, based on a blend of elastomers in accordance with the invention and comprising, as vulcanization accelerator, N-cyclohexyl-4,5-dihydro-2-thiazolesulphenamide (compound A), with the properties of several compositions not in accordance with the invention:

a first control composition comprising, as primary vulcanization accelerator, N-cyclohexyl-2-benzothiazole-sulphenamide ("CBS") and, as diene elastomer, solely natural rubber (composition 1), a second control composition comprising compound A as vulcanization accelerator and, as diene elastomer, solely natural rubber (composition 2), a third control composition comprising CBS as vulcanization accelerator and, as diene elastomers, a blend of natural rubber, polybutadiene and stirene/butadiene copolymer (thus a blend in accordance with the invention).

The formulations of the compositions are given in Table 1. The amounts are expressed as parts per 100 parts by weight of elastomer (phr).

TABLE 1

| Composition | 1 | 2 | 3 | 4 (according to the invention) |
|---|---|---|---|---|
| NR (1) | 100 | 100 | 40 | 40 |
| BR (2) | | | 20 | 20 |
| SBR (3) | | | 40 | 40 |
| N234 (4) | 54 | 54 | 54 | 54 |
| Paraffin | 1 | 1 | 1 | 1 |
| 6-PPD (5) | 2 | 2 | 2 | 2 |
| Stearic acid | 2 | 2 | 2 | 2 |
| ZnO | 2.7 | 2.7 | 2.7 | 2.7 |
| Sulphur | 1.1 | 1.1 | 1.1 | 1.1 |
| Vulcanization accelerator | 0.6* | 0.49** | 1.1* | 0.9** |

\* CBS ("Santocure" CBS from Flexsys)
\*\* N-cyclohexyl-4,5-dihydro-2-thiazolesulphenamide
(1) Natural rubber
(2) Polybutadiene with 0.7% of 1,2-, 1.7% of trans-1,4- and 98% of cis-1,4- (Tg = −105° C.) (molar %)
(3) Butadiene/stirene copolymer SSBR (SBR prepared in solution) with 25% of stirene, 59% of 1,2-poly-butadiene units and 20% of trans-1,4-polybutadiene units (Tg = −24° C.) (molar %); level expressed as dry SBR (SBR extended with 9% by weight of MES oil, i.e. a total of SSBR + oil equal to 76 phr)
(4) Carbon black N234
(5) Antioxidant 6-p-phenylenediamine Rubber composition 2 comprising N-cyclohexyl-4,5-dihydro-2-thiazolesulphenamide is identical to composition 1, it being understood that the CBS is replaced with an isomolar amount of N-cyclohexyl-4,5-dihydro-2-thiazolesulphenamide.

Rubber composition 4 comprising N-cyclohexyl-4,5-dihydro-2-thiazolesulphenamide is identical to composition 3, it being understood that CBS is replaced with an isomolar amount of N-cyclohexyl-4,5-dihydro-2-thiazolesulphenamide.

The rheometric properties at 150° C. and the reversion at 150° C. are given in Table 2.

TABLE 2

| 150° C./2 h | Comp. 1 (NR + CBS) | Comp. 2 (NR + A) | Comp. 3 (blend + CBS) | Comp. 4 (blend + A) |
|---|---|---|---|---|
| $t_o$ (min) | 4.9 | 3.7 | 6.1 | 3.7 |
| $\Delta$torque (dN · m) | 6.59 | 6.21 | 8.79 | 7.66 |
| $\Delta R_{120}$ | 19% | 28% | 10% | 0% |

It is noted that compositions 1 and 2 based on natural rubber which are not in accordance with the invention both exhibit significant reversion and in particular that composition 2 comprising compound A exhibits an even greater reversion than composition 1 comprising the accelerator normally used, which is CBS.

Furthermore, it is noted that, contrary to what composition 2 including compound A might have led it to be imagined, when the composition is based on a blend of natural rubber, polybutadiene and butadiene/stirene copolymer, the use of N-cyclohexyl-4,5-dihydro-2-thiazolesulphenamide (composition 4) makes it possible to obtain a reversion of 0%, which is a very great improvement with respect to composition 3 including CBS.

Furthermore, it is noted that compound A, and the compounds of formula (I) in general, advantageously replace, with regard to the environmental impact, sulphonamides comprising a mercaptobenzothiazole ring system, by not generating, in contrast to the latter, mercaptobenzothiazole on decomposing during the curing.

The invention claimed is:

1. A rubber composition for the manufacture of tires, based on a blend of at least one diene elastomer chosen from natural rubber and synthetic polyisoprene and of one or more diene elastomers chosen from the group consisting of polybutadienes, butadiene copolymers and isoprene copolymers, on one or more reinforcing fillers and on a vulcanization system, the said vulcanization system comprising one or more thiazoline compounds of formula:

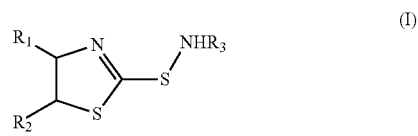

where $R_1$ and $R_2$ independently represent H or a C1-C25-hydrocarbon group chosen from linear, branched or cyclic alkyl groups and aryl groups, optionally interrupted by one or more heteroatoms, $R_3$ represents:

a linear or branched C1-C25 alkyl group which is optionally interrupted by one or more heteroatoms and which is optionally substituted by one or more cyclic C3-C10 alkyl or C6-C12 aryl groups, or a cyclic C3-C10 alkyl group which is optionally interrupted by one or more heteroatoms and which is optionally substituted by one or more linear, branched or cyclic C1-C25 alkyl or C6-C12 aryl groups which are optionally interrupted by one or more heteroatoms.

2. The composition according to claim 1, wherein $R_1$ and $R_2$ independently represent H or a methyl group.

3. The composition according to claim 2, wherein $R_1$ and $R_2$ each represent H.

4. The composition according to claim 1, wherein $R_3$ represents a cyclohexyl group or a tert-butyl group.

5. The composition according to claim 1, wherein the thiazoline compound or compounds represent from 0.1 to 10 phr.

6. The composition according to claim 1, wherein the blend is a blend of at least one diene elastomer chosen from natural rubber and synthetic polyisoprene with one or more polybutadienes and one or more butadiene/stirene copolymers.

7. The composition according to claim 1, wherein the reinforcing filler or fillers are chosen from silica, carbon black and their mixtures.

8. The composition according to claim 1, wherein the reinforcing filler or fillers are present at a level of between 20 and 200 phr.

9. A process for preparing a rubber composition for the manufacture of tires as defined in claim 1, comprising the steps of:

incorporating the reinforcing filler or fillers in the diene elastomers, during a first "non-productive" stage, everything being kneaded thermomechanically, in one or more goes, until a maximum temperature of between 130° C. and 200° C. is reached, cooling the combined mixture to a temperature of less than 100° C., subsequently incorporating, during a second "productive" stage, the vulcanization system and then kneading everything up to a maximum temperature of less than 120° C.

10. A process for manufacturing a finished article or a semi-finished product intended for a motor vehicle ground-contact system comprising incorporating a composition according to claim 1.

11. Finished article or semi-finished product intended for a motor vehicle ground-contact system, comprising a composition according to claim 1.

12. Tire, comprising a rubber composition as defined in claim 1.

13. A process for preparing a composition based on a blend of at least one diene elastomer selected from the group consisting of natural rubber and synthetic polyisoprene and of one or more diene elastomers selected from the group consisting of polybutadienes, butadiene copolymers and isoprene copolymers, on one or more reinforcing fillers and on a vulcanization system, comprising incorporating in the composition, as a vulcanization accelerator, one or more thiazoline compounds of formula (I) as defined in claim 1.

14. The composition according to claim 1, wherein the thiazoline compound or compounds represent from 0.5 to 7 phr.

15. The composition according to claim 1, wherein the thiazoline compound or compounds represent from 0.5 to 5 phr.

16. The composition according to claim 1, wherein the reinforcing filler or fillers are present at a level of between 30 and 150 phr.

* * * * *